(12) United States Patent
Lin et al.

(10) Patent No.: US 11,166,746 B2
(45) Date of Patent: Nov. 9, 2021

(54) INTEGRATED DEVICE FOR HAIR FOLLICLE EXTRACTION AND IMPLANTING

(71) Applicant: Shantou University, Guangdong (CN)

(72) Inventors: Changmin Lin, Guangdong (CN); Shaoke Chen, Guangdong (CN); Keng Huang, Guangdong (CN); Haihong Li, Guangdong (CN); Hanmin Huo, Guangdong (CN); Junwei Huang, Guangdong (CN); Cheng Yang, Guangdong (CN); Zhuoying Yu, Guangdong (CN); Zhiwen Chen, Guangdong (CN); Lingli Kong, Guangdong (CN); Haibin Chen, Guangdong (CN); Shaoqin You, Guangdong (CN); Haixia Ma, Guangdong (CN); Zhenping Li, Guangdong (CN); Xiaoyun Zhang, Guangdong (CN); Xin Chen, Guangdong (CN)

(73) Assignee: Shantou University, Shantou (CN)

( * ) Notice: Subject to any disclaimer, the term of this patent is extended or adjusted under 35 U.S.C. 154(b) by 327 days.

(21) Appl. No.: 16/392,695

(22) Filed: Apr. 24, 2019

(65) Prior Publication Data
US 2019/0247089 A1 Aug. 15, 2019

Related U.S. Application Data

(63) Continuation of application No. PCT/CN2017/089070, filed on Jun. 19, 2017.

(30) Foreign Application Priority Data

Oct. 25, 2016 (CN) .......................... 201610932801.0

(51) Int. Cl.
*A61B 17/34* (2006.01)
*A61F 2/10* (2006.01)
(Continued)

(52) U.S. Cl.
CPC .......... *A61B 17/3468* (2013.01); *A61B 17/00* (2013.01); *A61B 17/32* (2013.01);
(Continued)

(58) Field of Classification Search
CPC ..... A61B 17/3468; A61B 17/00; A61B 17/32; A61B 17/3205; A61B 17/32053;
(Continued)

(56) References Cited

U.S. PATENT DOCUMENTS

2007/0078475 A1* 4/2007 Bodduluri .............. A61B 90/36
606/187
2009/0088720 A1* 4/2009 Oostman, Jr. .......... A61B 34/30
604/403
(Continued)

FOREIGN PATENT DOCUMENTS

CN 206675548 U 11/2017

*Primary Examiner* — Erich G Herbermann

(57) ABSTRACT

The present invention relates to an integrated device for hair follicle extraction and implanting, comprising a body mechanism and a connecting mechanism, the body mechanism comprising a body supporting frame, a first motor, a transmission frame, a second motor, a clamping component, a transmission mechanism and a pushing needle, the connecting mechanism comprises a connecting head, a fixing head and a cutter head, wherein the first motor of the body mechanism controls the up and down movement of the cutter head through the cooperation of the transmission frame and the transmission mechanism, and the second motor controls the pushing needle by the rotary motion of the clamping unit, simultaneously controls the rotational movement of the cutter head through the transmission mechanism. Compared with the prior art, the invention
(Continued)

realizes the integrated operation of hair follicle extracting and implanting, and makes the operation of hair follicle implanting more convenient.

15 Claims, 14 Drawing Sheets

(51) Int. Cl.
*A61B 17/3205* (2006.01)
*A61B 17/32* (2006.01)
*A61B 17/00* (2006.01)

(52) U.S. Cl.
CPC .... *A61B 17/3205* (2013.01); *A61B 17/32053* (2013.01); *A61F 2/10* (2013.01); *A61B 2017/00743* (2013.01); *A61B 2017/00752* (2013.01); *A61B 2017/00969* (2013.01); *A61B 2017/320064* (2013.01)

(58) Field of Classification Search
CPC ...... A61B 17/3403; A61B 2017/00743; A61B 2017/00752; A61B 2017/00969; A61B 2017/320064; A61B 2017/3405; A61B 2017/0002; A61B 90/11; A61F 2/10
See application file for complete search history.

(56) References Cited

U.S. PATENT DOCUMENTS

2009/0178943 A1* 7/2009 Oostman, Jr. .......... A61B 34/30
                                                                                     206/438
2017/0143434 A1* 5/2017 Jung .................. A61B 17/3468

* cited by examiner

E–E

INTEGRATED DEVICE FOR HAIR FOLLICLE EXTRACTION AND IMPLANTING

CROSS REFERENCE TO RELATED APPLICATIONS

The present application is a Continuation Application of PCT Application No. PCT/CN2017/089070 filed on Jun. 19, 2017, which claims the benefit of Chinese Patent Application No. 201610932801.0 filed on Oct. 25, 2016. All the above are hereby incorporated by reference.

FIELD OF THE INVENTION

The present invention discloses an integrated device for hair follicle extraction and implanting.

BACKGROUND OF THE INVENTION

The invention relates to the field of medical instruments, in particular to an integrated device capable of hair follicle extraction and implanting.

Hair transplantation is the most widely used medical surgery for saving hair loss. The surgery removes the hair follicle from a specific body part of the patient, then after separation and selection, the removed hair follicle is transplanted to the patient's body part of hair loss. The traditional hair transplantation surgery uses implanting or perforating knives and medical forceps. The method of extracting hair follicle is generally to separate the hair follicle from the scalp and then use medical tweezers. There are two methods for planting hair follicle. One method is first placing the hair follicle in the implanting needle, use the implanting needle to punch the hole in the implanting area and press the button on the implanting needle to complete the perforation implanting. The disadvantage is that the needle is easy to passivate and has a short service life. Another method is more common, the hole is first punched with a punching knife, and then the hair follicle is implanted in the hole with tweezers. The disadvantage of this method is that the number of operation steps is increased and the hole punched by the perforating knife is small, which makes the operation difficult to handle. Traditional hair transplantation surgery is inefficient and costly because of the limitations of the device.

SUMMARY OF THE INVENTION

The object of the present invention is to provide an integrated device for extraction and implanting hair follicle, so as to solve the problems of using a plenty of instruments for extraction and implanting hair follicle in the prior art, of which steps are cumbersome, and the hair follicle is easy to be damaged.

In order to solve the above problems, the present invention adopts the following technical solutions: An integrated device for hair follicle extraction and implanting, which comprises a body mechanism and a connecting mechanism, the body mechanism comprising a body supporting frame, a first motor, a transmission frame, a second motor, a clamping member, a transmission mechanism and a pushing needle; wherein the first motor is fixed inside the body supporting frame, the first motor is connected to the transmission frame; the second motor is fixed inside the body supporting frame, and the motor shaft of the second motor is connected to the pushing needle through the clamping member; the transmission mechanism comprises a sleeve and a clamping sleeve, the sleeve is connected with the clamping member, the sleeve is matched with the clamping sleeve in the transmission process, and a gap capable of up-and-down movement is provided between the sleeve and the clamping sleeve; the connecting mechanism comprises a connecting head, a fixing head, and a cutter head, the connecting head is connected with the body supporting frame, and the fixing head is connected with the connecting head; the cutting head is hollow inside, and the pushing needle is placed in the cutting head, the cutting head penetrates through the connecting head and the fixing head, and the upper part of the cutting head is connected to the clamping sleeve; the sleeve is connected to the clamping sleeve, the first motor drives the cutter head to move up and down, and the second motor drives the rotary motion of the pushing needle and the cutter head.

The invention is equivalent to the hair follicle transplanting pen, which can complete the extraction and implanting of hair follicle in turn, the first motor drives the cutter head to move up and down through the transmission frame, the second motor controls the rotation of the pushing needle in the cutter head, and the design and the connection of the clamping member and the transmission drive the rotation of the cutter head. When extracting the hair follicle, start the second motor, rotate the cutter head, drill into a suitable depth and stop the operation, then start the first motor, push the cutter head down, the cutter head is hollow, then the hair follicle is extracted and placed in the hollow space of the cutter head, and pull out the cutter head. When implanting the hair follicle, start the second motor, rotate the cutter head to the appropriate depth and stop the operation, then start the first motor, and the cutter head is lifted upward. Since the pushing needle does not move, the cutter head is lifted relative to the pushing needle, and the hair follicle is pushed by the pushing needle, realizing hair follicle implanting.

According to the present invention, the first motor is a stepping motor, the second motor is a direct current brushless motor. The stepping motor can change the movement distance of the cutter head up and down by changing the number of electronic coils. Direct current brushless motor brings good stability, precise control, and controllability, which is better than a normal motor. It can realize frequency conversion control and ease regulation to speed.

According to the present invention, the body supporting frame is divided into a first supporting frame and a second supporting frame that connected to each other; the first motor is fixed in the first supporting frame by a fixing member, the second motor is fixed on the second supporting frame by a fixing scaffold; the connecting head is connected with the second supporting frame in the body supporting frame. The first supporting frame is provided at the upper portion of the body supporting frame, and the second supporting frame is provided at the lower portion of the body supporting frame. The first supporting frame and the second supporting frame are connected by a screw.

According to the present invention, the fixing member comprises two fixing units placed symmetrically, the first motor is sandwiched by the two fixing units, the fixing member is connected with the first supporting frame. The inner diameter of the two fixing units is slightly smaller than the maximum outer diameter of the first motor, and the two fixing units are fixed by screws and nuts to ensure that the first motor is fixed, and the fixing member is matched with the first supporting frame by screws, and the first motor is fixed at the inside of the first supporting frame.

According to the present invention, a position limiting key is placed between the fixing scaffold and the second supporting frame; the position limiting key is stuck on the second supporting frame, so as that the fixing scaffold is fixed on the second supporting frame.

According to the present invention, the transmission frame is hollow in the vertical direction, the position limiting key penetrates through the hollow part of the transmission frame to restrict the rotation of the transmission frame. The transmission frame is of hollow cylindrical shape, and the transmission frame is placed between the second motor and the second supporting frame. For the assembly of the position limiting key, the position limiting key is inserted through the corresponding opening on the second supporting frame, and the middle part of the position limiting key is in the hollow position of the transmission frame, and the transmission frame is restricted to rotate. While the top of the position limiting key is inserted into the corresponding slot of the fixing scaffold. Hence, the transmission frame can move up and down rather than can be rotated.

According to the present invention, the connecting head is in flexible connection with the body supporting frame, the connecting mechanism is detachable from the body mechanism.

For the flexible connection, the connecting head comprises an upper clamping unit, a spring and a clamping key, a lower clamping unit; the upper clamping unit is matched with the lower clamping unit and fixed inside the connecting head; the clamping key is sleeved with a spring, and the clamping key is fixed in a protruding position between the upper clamping unit and the lower clamping unit; an opening is formed in the outer wall of the body supporting frame, a protruding portion of the clamping key is clamped in the opening of the body supporting frame, which brings the clamping key in fixed connection with the connecting mechanism. The spring is always in a compressed state, and the clamping key is kept in protruding state under the elastic force, and the clamping key can be moved between the upper clamping unit and lower upper clamping unit. When the connecting mechanism is to be separated from the body mechanism, the clamping key is pressed to compress the spring, and the clamping key is disassembled from the opening in the outer wall of the body supporting frame, then the connecting mechanism is separated from the body mechanism. Once the separation is completed, the clamping key is released, and the clamping key returns to the original state under the elastic force of the spring. The connecting mechanism is movably connected to the second supporting frame through the clamping key, and the remaining part of the connecting mechanism is not connected with the second supporting frame except that the clamping key is in a flexible connection with the second supporting frame.

According to the present invention, a groove structure is provided at the periphery of the connecting head, and the groove structure is disposed at the joint part between the connecting head and the body supporting frame. When the groove structure is used for separation, accessories can be clamped in the groove structure for ease of disassembly and separation. After the connecting mechanism is connected with the body mechanism, a portion of the connecting head protrudes from the body supporting frame, and the groove structure is provided at the protruding portion.

According to the present invention, the connecting head further comprises a clamping unit, the clamping unit is disposed between the clamping key and the cutter head, and the clamping unit is connected to the clamping key, and the clamping unit clamps the cutter head as the clamping key is retracted. The clamping unit and the clamping key are in screw connection. For disassembly, the clamping key is retracted and the clamping unit is pressed at the same time, the clamping unit clamps the cutter head, and entire of the connecting mechanism including the cutter head is separated.

According to the present invention, a plurality of the connecting mechanism can be provided, and the connecting mechanism may be separated as a whole from the body mechanism. After the hair follicle is extracted, the cutting head and the extracted hair follicle are taken out along with the connecting mechanism for storage, and the connecting mechanism without the hair follicle is loaded on the body mechanism for the continuing work of extracting hair follicle. After implanting the hair follicles, the connecting mechanism without hair follicle is taken out, and the connection mechanism storing hair follicle is loaded to continue implanting work. The hair follicle extraction and implanting are carried out in steps to improve work efficiency.

According to the present invention, the interior of the fixing head is of an inverted cone shape and a hollow structure with a wide upper portion and a narrow lower portion, a plurality of cutting edges are arranged at the lower part of the cutting head, and the cutting edges are bent towards the inside of the cutting head. The design of inverted cone shape inside the fixed head allows the cutter tip of the cutter head to cut hair follicle slowly as the cutter head is moving downward, then the fixing head is in a closed state to prevent the hair follicle from falling out. With the distances change between the upper and lower part of the cutter head, the closing degree of the cutter tip is different, the cutter tip is at an angle with the cutter head, and the cutter tip is bent inward to increase the success rate of extraction since the hair follicle is extracted by cutting instead of the extrusion method. The cutter head is hollow and can store the cut hair follicle and provide moving space for the pushing needle. The pushing needle is a solid cylindrical body which is thick in upper part and thin in lower part, and the pushing needle is connected to the second motor through the clamping unit. When the first motor is operated, the pushing needle is fixed when the cutter head moves upward, and the hair follicle can be pushed out.

According to the present invention, the sleeve is of an external spline structure, and the upper portion of the clamping sleeve is of an internal spline structure, and the clamping sleeve is in transmission match with the sleeve, and the lower portion of clamping sleeve is connected with the upper portion of the cutter head. The inner portion of the sleeve is in an interference fit with the clamping member, so that the clamping member can hold the pushing pin more tightly and enables it to transmit the rotational motion of the second motor to the sleeve. The spline structure between the clamping sleeve and the sleeve enables the clamping sleeve to rotate as the sleeve rotates. At the same time, there is a gap between the upper portion of the sleeve and the clamping sleeve to ensure that the clamping sleeve can move up and down relative to the sleeve. During the movement of the clamping sleeve according to the up and down movement of the transmission frame, the clamping sleeve can acquire the driving force from the rotary motion of the DC motor.

According to the present invention, the clamping sleeve is connected with the upper portion of the cutter head through a gear sleeve, and the gear sleeve is of an inner gear sleeve, the upper part of the cutter head is provided with a straight gear, and the inner gear sleeve is in meshed connection with the straight gear. The gears transmit the rotary motion from the clamping sleeve to the cutter head.

According to the present invention, the gear sleeve is made of an elastic material, the inner gear is of an inverted triangle shape, and the top of the gear is rounded. The inverted triangular structure of the inner gear makes it can auto-adjust when the cutter head enters, ensures its cooperation with the cutter head, and uses its own elastic property to clamp cutter head, and the inner gear sleeve simultaneously plays the role of transmission and clamping.

According to the present invention, the integrated device for hair follicle extraction and implanting further comprises a foot part switch and a hand part button, the foot part switch is provided at the outside of the body mechanism to connect and control the second motor, the hand part button is provided on the body mechanism to connect and control the second motor. The hand part button includes an upper patching button and a lower patching button, the upper patching button controls the first motor to move upward, and the lower patching button controls the first motor to move downward.

Compared with the prior art, the present invention realizes the integrated operation of extracting and implanting, which makes the operation of hair follicle implanting more convenient. The cutter head can realize drilling, cutting the hair follicle, storing the hair follicle, and cooperating with the pushing needle to realize implanting hair follicle. Compared with the traditional hair follicle extraction and implanting methods, the medical effect of the present invention is better, in detail, the damage to the hair follicle is smaller, and the planting success rate is higher. It also achieves a step-by-step mode of extracting and implanting, which is flexible in operation and it can be adapted to different requirements of operation.

BRIEF DESCRIPTION OF THE DRAWINGS

FIG. 12, FIG. 13 and FIG. 14 are structural views of a connecting head when the connecting mechanism is removed, wherein FIG. 12 is a front view of the connecting mechanism when it is removed, and FIG. 13 is a top view of the connecting mechanism when the upper clamping unit is removed, FIG. 14 is a top view of the clamping state of the clamping unit in FIG. 13;

FIG. 15, FIG. 16 and FIG. 17 are structural views of the connecting head when the connecting mechanism is restored, wherein FIG. 15 is a front view of the connecting mechanism when the connecting mechanism is restored, and FIG. 16 is a plan view of the connection mechanism after the removal of the upper clamping unit, FIG. 17 is a top view of the clamped unit in a released state.

DETAILED DESCRIPTION OF ILLUSTRATED EMBODIMENTS

The present invention will be further described in detail below with reference to the accompanying drawings and specific embodiments. The following examples are intended to illustrate the invention but are not intended to limit the scope of the invention.

Example 1

Figure 1:
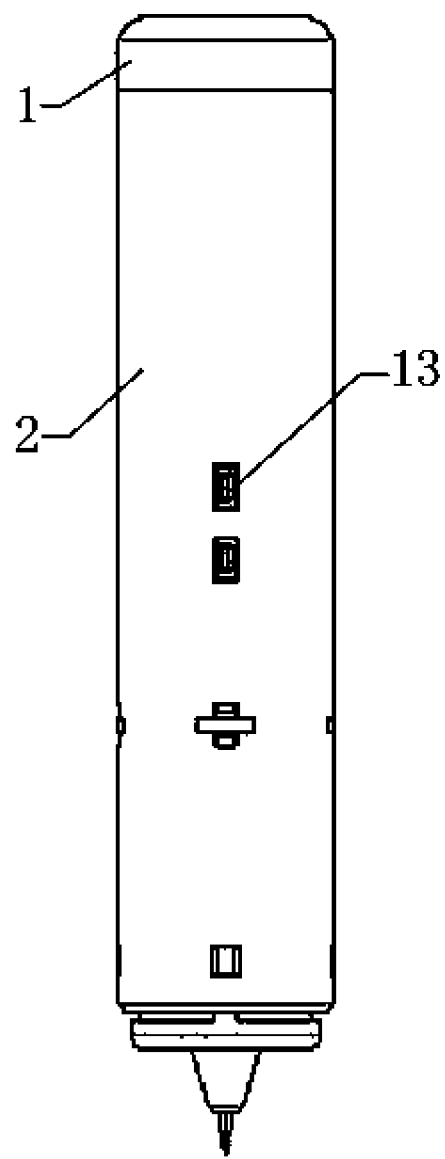
FIG. 1 is a schematic view of the present invention.

The integrated device for hair follicle extraction and implanting of the present invention has a shape similar to that of the pen. As shown in FIG. 1, an integrated device for hair follicle extraction and implanting, which comprises a body mechanism and a connecting mechanism. The body mechanism is the holding portion, and the outer casing is a body supporting frame, including a first supporting frame 1 and a second supporting frame 2. The first supporting frame 1 and the second supporting frame 2 are screwed into connection with each other, forming the body supporting frame of pen-shape. the connecting mechanism is in clamping connection with the second supporting frame 2. The connecting head is in a flexible connection with the body supporting frame, the connecting mechanism is detachable from the body mechanism. As shown in FIG. 2-5, the connecting mechanism comprises a connecting head 3, a fixing head 4 and a cutter head 5, the fixing head 4 is connected with the connecting head 3, the connecting head 3 is in a flexible connection with the second supporting frame 2, hence, the connecting mechanism is detachable from the body mechanism. The connecting head 3 comprises an upper clamping unit 31, a spring 32 and a clamping key 33, a lower clamping unit 34; the upper clamping unit 31 is matched with the lower clamping unit 34 and fixed inside the connecting head 3; the clamping key 33 is sleeved with the spring 32, and the clamping key 33 is fixed in a protruding position between the upper clamping unit and the lower clamping unit; an opening is formed in the outer wall of the body supporting frame, a protruding portion of the clamping key is clamped in the opening of the second supporting frame 2, which bring the clamping key 33 in fixed connection with the connecting mechanism. As shown in FIG. 12-17, The clamping unit 35 is placed between the clamping key 33 and the cutter head 5, and the clamping unit 35 is connected to the clamping key 33, and the clamping unit 35 clamps the cutter head 5 as the clamping key 33 is retracted. The clamping unit 35 and the clamping key 33 are in screw connection. For disassembly, the clamping key 33 is retracted and the clamping unit 35 is pressed at the same time, the clamping unit 31 clamps the cutter head 5, and entire of the connecting mechanism 2 including the cutter head 5 is separated.

A groove structure 36 is provided at the periphery of the connecting head 3, and the groove structure 36 is disposed at the joint part between the connecting head 3 and the body supporting frame 2.

Figure 2:
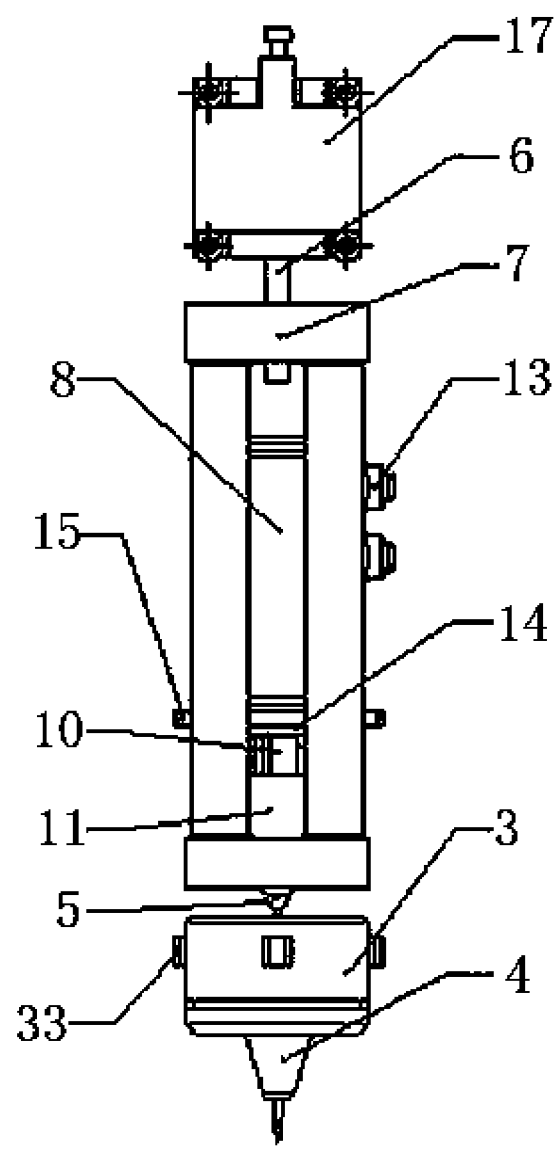
FIG. 2 is a schematic view of an integrated device for hair follicle extraction and implanting without the body supporting frame according to the present invention.
Figure 3:
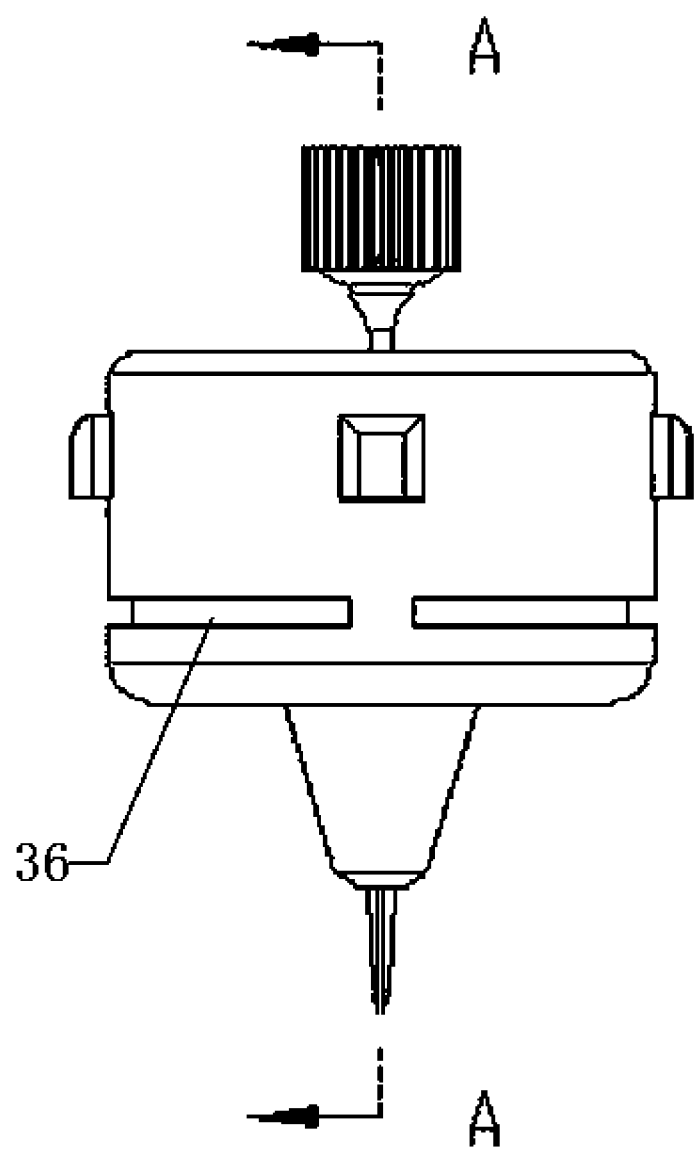
FIG. 3 is a schematic view of the structure of a connecting mechanism according to the present invention.
Figure 4:
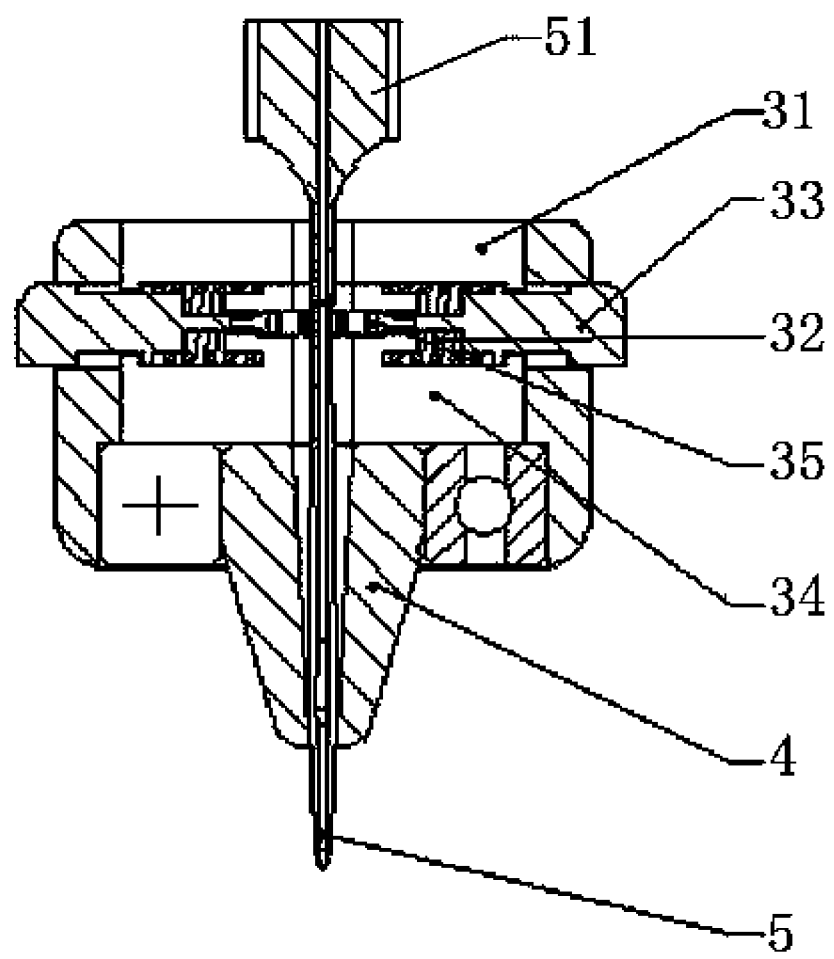
FIG. 4 is a cross-sectional view showing a connecting mechanism according to the present invention.
Figure 5:
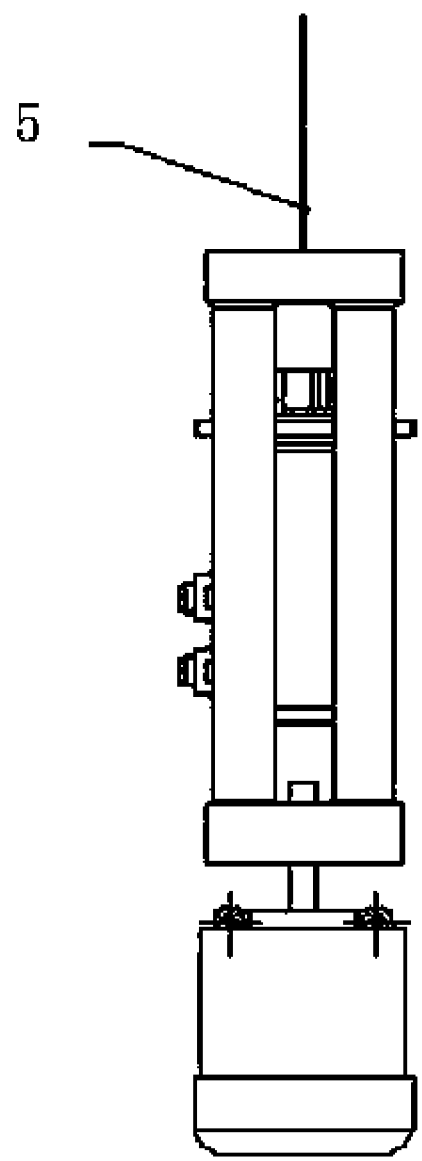
FIG. 5 is a schematic view of the structure of the body mechanism according to the present invention.
Figure 10:
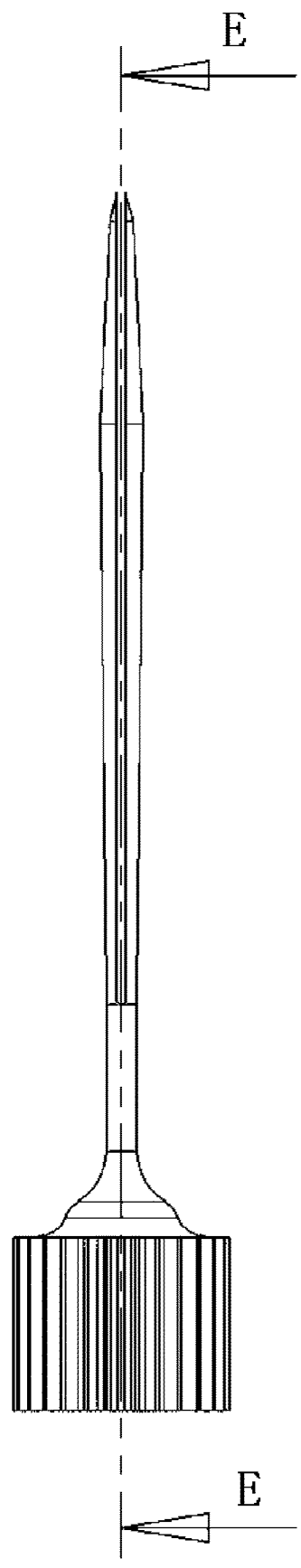
FIG. 10 is a structural view of a portion of the cutter head according to the present invention.
Figure 11:
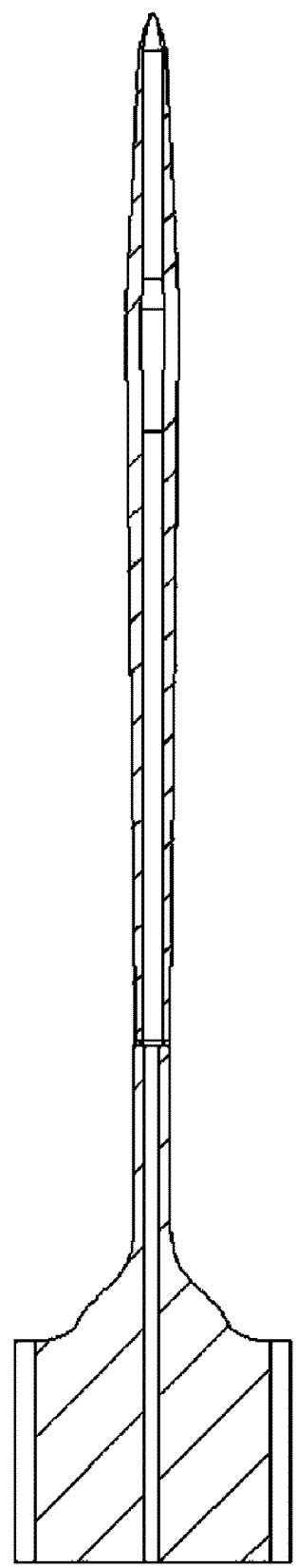
FIG. 11 is a cross-sectional view of FIG. 10.
Figure 12:
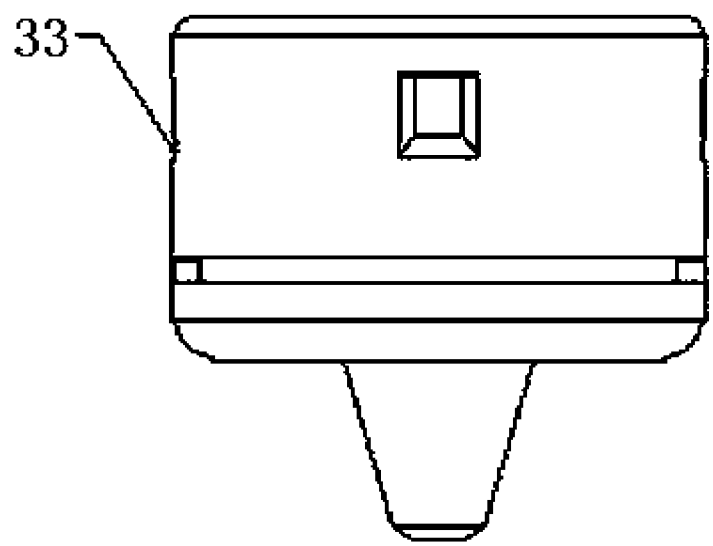
Figure 13:
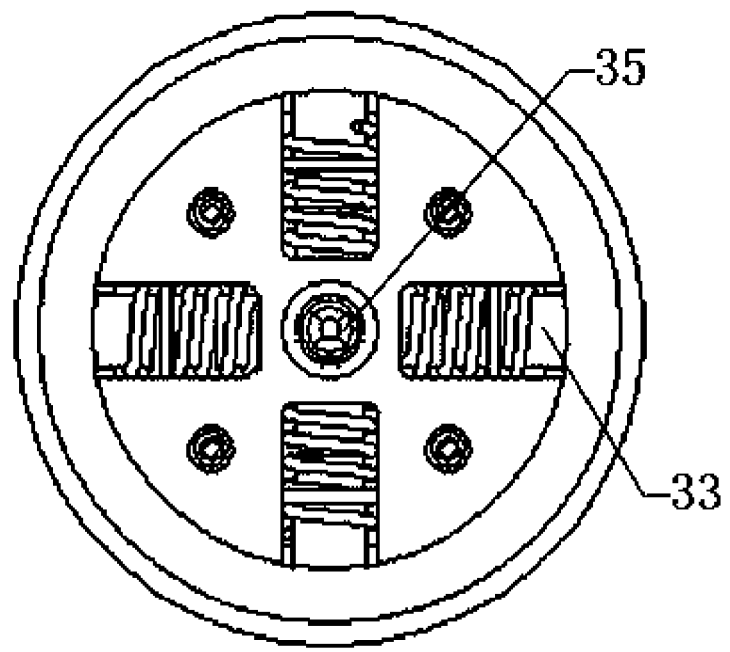
Figure 14:
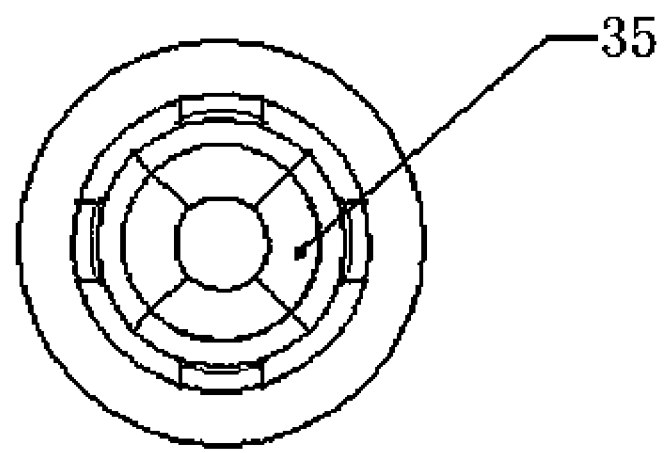
Figure 15:
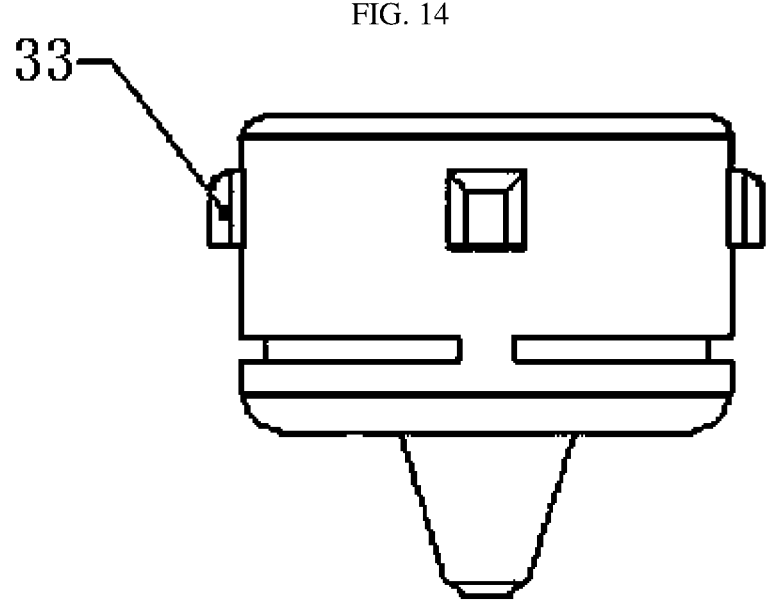
Figure 16:
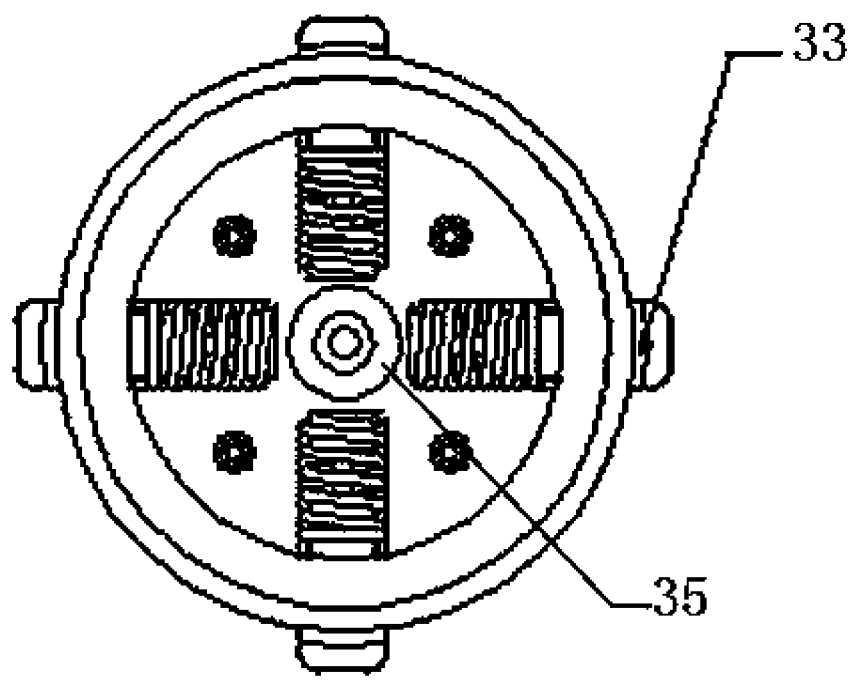
Figure 17:
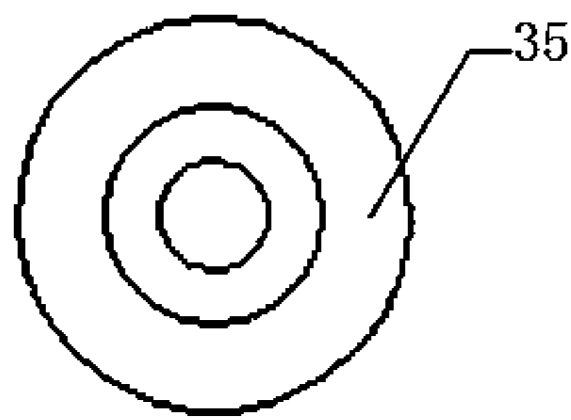

The fixing head 4 is of an inverted cone shape and a hollow structure with a wide upper portion and a narrow lower portion. As shown in FIGS. 2, 10 and 11, the upper part of the cutter head 5 is provided with a straight gear 51, and a plurality of cutting edges are arranged at the lower part of the cutting head 5, and the cutting edges are bent towards the inside of the cutting head. When the tip of the cutting head is bent inside the cutter head and the cutter head 5 moves downward relative to the fixing head 4, the cutter head 5 is pressed and closed.

Figure 6:
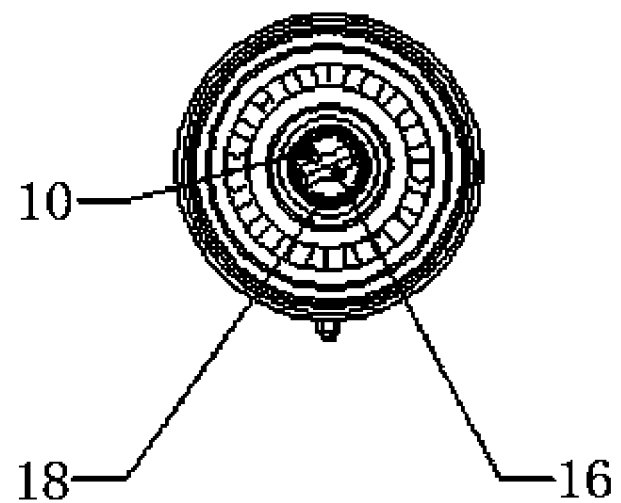
FIG. 6 is a transverse cross-sectional view of the body mechanism according to the present invention.
Figure 7:
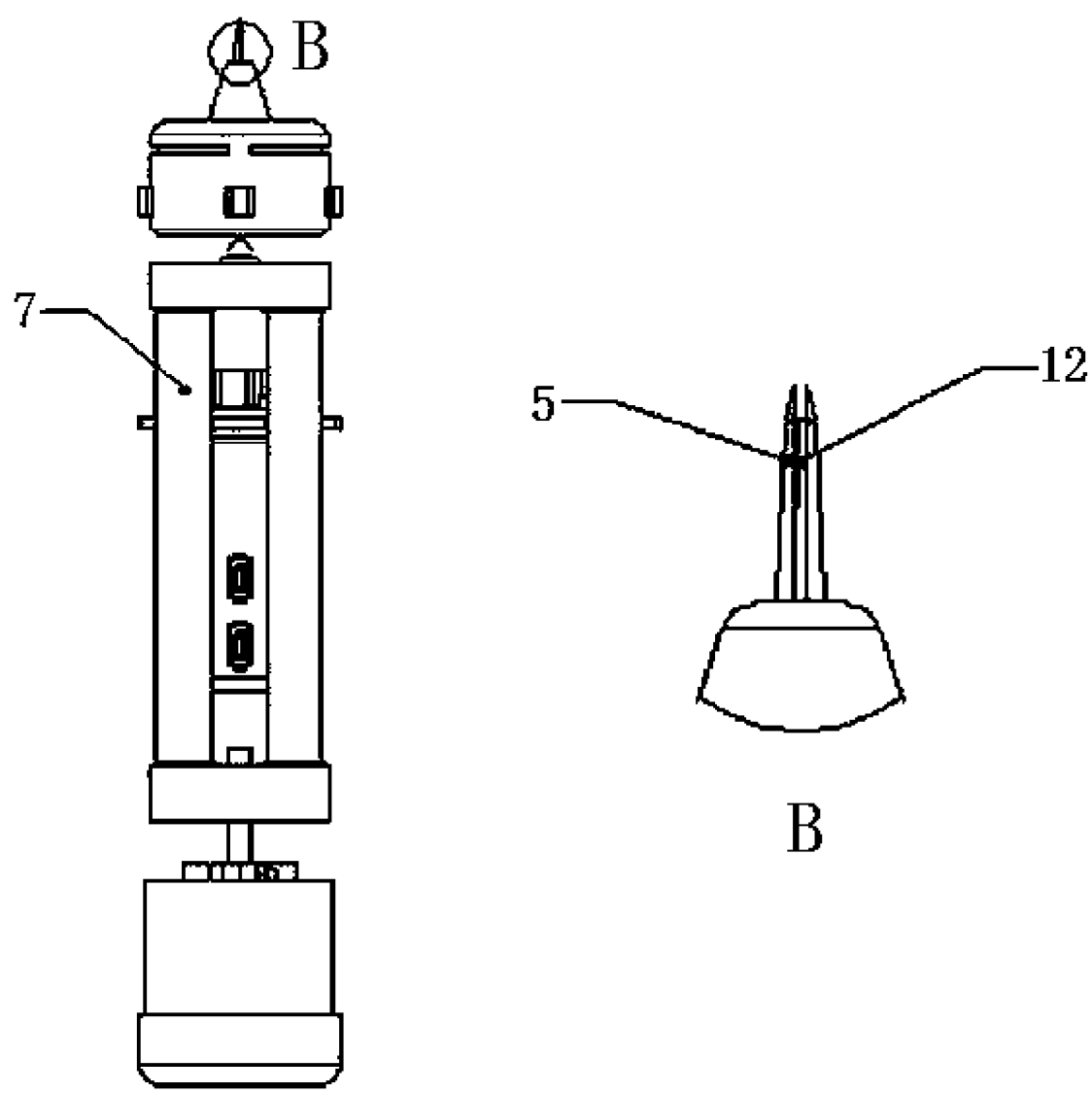
FIG. 7 is a structural view of the present invention in the initial state and a partial view of the cutter head in the initial state.
Figure 8:
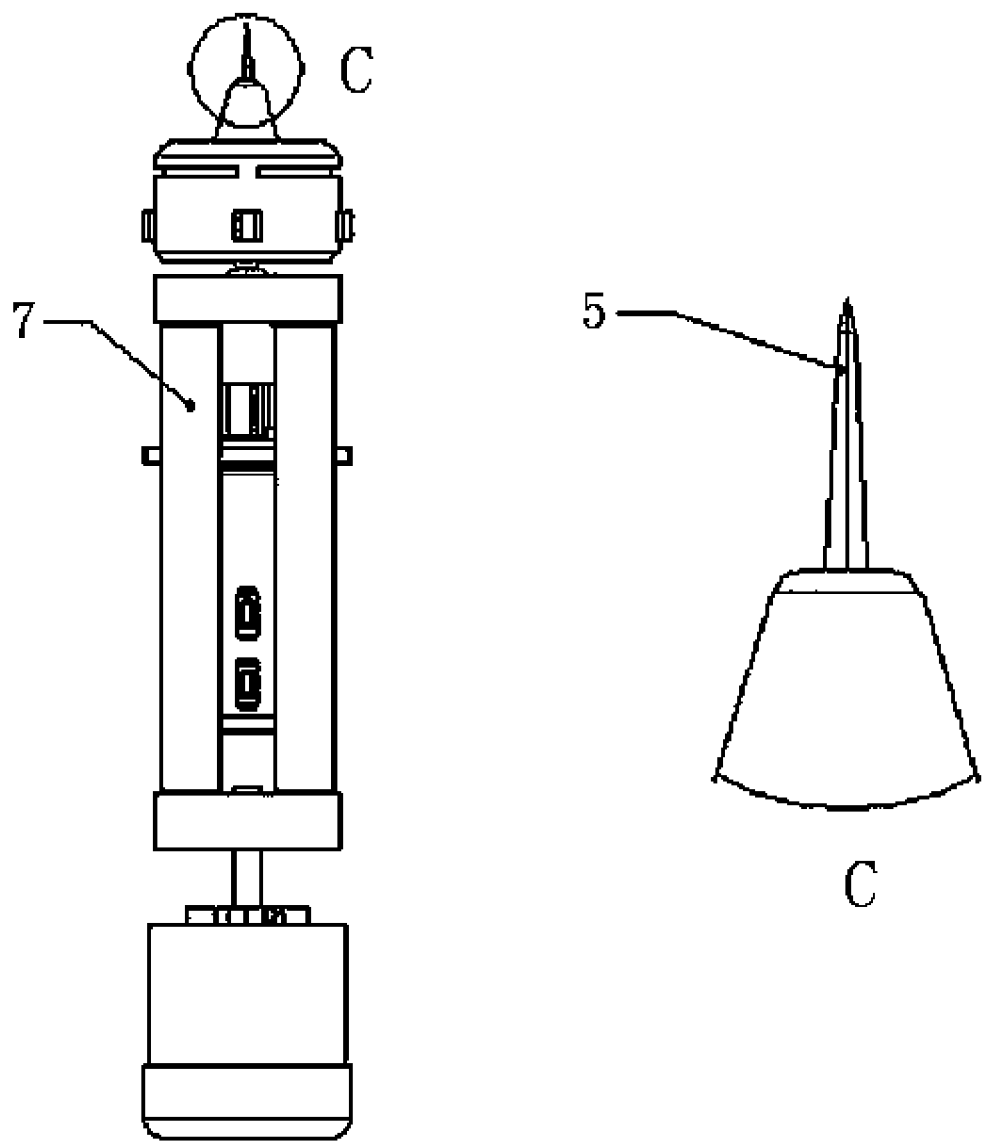
FIG. 8 is an integrated device in the extraction state of the present invention and a partial view of the cutter head when the hair follicle is extracted.
Figure 9:
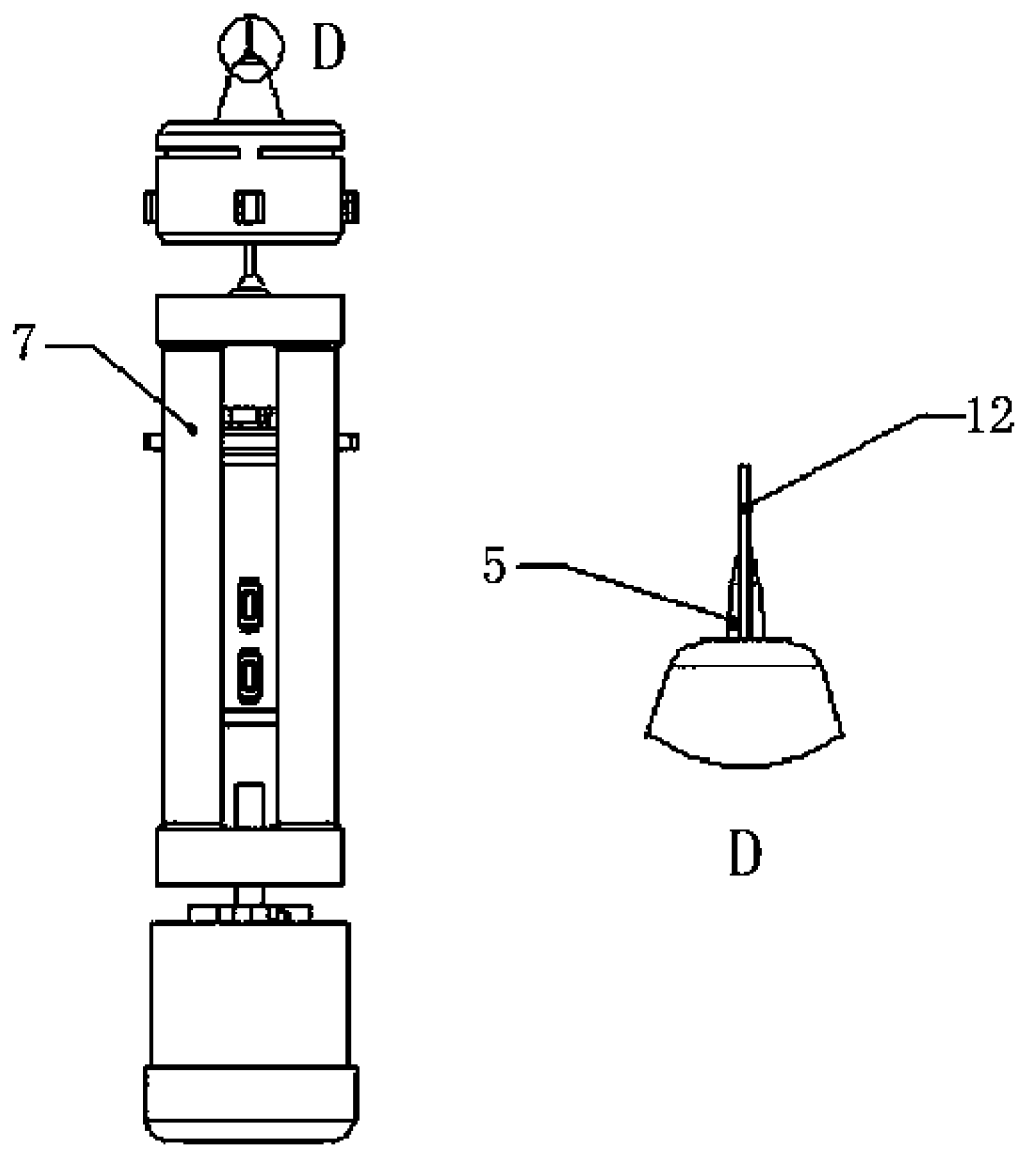
FIG. 9 is an integrated device in the implanting state of the present invention and a partial view of the cutter head when the hair follicle is implanted.

As shown in FIGS. 2, 7, 8 and 9, the body supporting frame 1 includes a stepping motor 6, a transmission frame 7, a DC brushless motor 8, a clamping member 9, a sleeve 10, a clamping sleeve 11, a pushing needle 12, and a patching button 13. The brushless DC motor 8 is fixed on a fixing scaffold 14, and the fixing scaffold 14 is fixed on the second supporting frame 2 by a position limiting key 15, as shown in FIG. 2 and FIG. 6, the DC brushless motor 8 and the pushing needle 12 are connected by two clamping units. a position limiting key 15 is placed between the fixing scaffold 14 and the second supporting frame 2; the position limiting key 15 is stuck on the second supporting frame, so as that the fixing scaffold 15 is fixed on the second supporting frame 2. The inner portion of the sleeve 10 is in an interference fit with two clamping units 16, so that the clamping units 16 can hold the pushing needle 12 more tightly and enables it to transmit the rotational motion of the second motor to the sleeve. The sleeve 10 is of an external spline structure, and the upper portion of the clamping sleeve 11 is of an internal spline structure, and the clamping sleeve 11 is in transmission match with the sleeve 10. At the same time, there is a gap between the upper portion of the sleeve 10 and the clamping sleeve 11 to ensure that the clamping sleeve 11 can move up and down relative to the sleeve 10. During the movement of the clamping sleeve according to the up and down movement of the transmission frame, the clamping sleeve can acquire the driving force from the rotary motion of the DC motor. The periphery of the brushless DC motor 8 is the transmission frame 7, and the transmission frame 7 and the second supporting frame 2 are not connected or contacted. The stepping motor 6 is fixed inside the first supporting frame 1 by a fixing member 17 comprises two fixing units 17 placed symmetrically, the stepping motor 6 is sandwiched by the two fixing units 17 at the inside of the first supporting frame 1. The inner diameter of the two fixing units 17 is slightly smaller than the maximum outer diameter of the stepping motor 6, and the two fixing units 17 is fixed by screws and nuts to ensure that the stepping motor 6 is fixed, and the fixing member 17 is matched with the first supporting frame 1 by screws. The stepping motor 6 is connected to the clamping sleeve 11 through the transmission frame 7 to control the up and down movement of the cutter head 5. The clamping sleeve 11 is connected with the straight gear 51 on the upper portion of the cutter head 5 through a gear sleeve 18, and the gear sleeve 18 is of an inner gear sleeve, the inner gear is an inverted triangle, the top of the tooth is rounded, and the gear sleeve 18 is in meshed connection with the straight gear 51. The gears transmit the rotary motion from the clamping sleeve to the cutter head. The gear sleeve 18 is an elastic material. When disassembly, the clamping member 35 clamps the cutter head 5, and the cutter head 5 is separated with the connecting member. The patching button 13 is provided on the second supporting frame to connect and control the motor. The patching button includes an upper patching button and a lower patching button, the upper patching button controls the first motor to move upward, and the lower patching button controls the first motor to move downward. In order to facilitate the control, a foot switch is also provided, and the foot switch is disposed outside the body mechanism to connect and control the DC brushless motor 8.

The working principle of the integrated device for hair follicle extraction and implanting will be briefly described below with reference to the accompanying drawings.

For the extraction of the hair follicle, the operator holds the integrated device in the hand, puts the integrated device on the targeted position, and starts the DC brushless motor with the foot switch. If the integrated device is in the state after implanting, the stepping motor 6 will automatically start first, so that the integrated device returns to the initial state. Then, the DC brushless motor 8 is restarted, then the cutter head 5 is drilled to a suitable depth, and the patching button 16 is pressed, so that the DC brushless motor 8 stops moving, and then the stepping motor 6 is started to push the transmission frame 7 forward, the transmission frame 7 drives the clamping sleeve 11 to move downward, and the clamping sleeve 11 is fixed with the cutter head 5, the cutter head 5 is downward, the fixing head 4 is fixed, and the cutter head 5 moves downward relative to the fixing head. The interior of the fixing head is of a hollow structure with a wide upper portion and a narrow lower portion, the cutter head 5 is closed after being moved downward for a certain distance, and the inner diameter of the fixing head 4 turns smaller, and the tip the cutter head 5 is closed, so that the hair follicle is obliquely cut at an angle and stored inside the cutter head 5 in closed state.

For implanting hair follicle, the operator holds the integrated device in the hand, puts the integrated device in the targeted position, starts the DC brushless motor 8 with the foot switch, then drills the cutter head 5 to the appropriate depth, and presses the patching button 13 at the top position. The DC brushless motor 8 stops moving, then the stepping motor 6 starts to drive the transmission frame 7 to retreat, the transmission frame 7 drives the clamping sleeve 11 to move upward, and the clamping sleeve 11 is fixed with the cutter head 5, whereby the cutter head 5 moves downward. The fixing head 4 is fixed, and the cutting head 5 moves upward relative to the fixing head 4. The fixing head 4 has an inner structure with a wide upper portion and a narrow lower portion, and the cutter head 5 is loosened after the diameter of the fixing head 4 becomes larger after moving downward for a certain distance. The cutter tip portion of the cutter head 5 is closed, and the push pin 12 is indirectly fixed to the motor shaft of the DC brushless motor 8, and does not move with the carriage 7, and after the cutter head 5 retreats and opens the closed cutter tip, the pushing needle 12 is pushed. The hair follicles stored inside the cutter head 5 are pushed out to improve the success rate of hair follicle implanting.

For the disassembly of the connecting mechanism, the groove structure 36 under the connecting head 3 is first clamped by the appliance, and then the lower joint is rotated by the fixture to hold the protruding position, so that the clamping key 33 is contracted, and the clamping unit 35 shrinks and clamps the cutting head 5, then pull out the whole of the connection mechanism. After the connection mechanism leaves the body mechanism, the spring 32 pushes the clamping key 33 to return to the original position, and the clamping key 33 drives the clamping member 35 back to the original position. After the integrated device is separated, the body mechanism automatically starts the stepping motor, so that the body mechanism returns to the initial state.

When the connecting mechanism is restored, the body mechanism is first returned to the same state as the connection. If the connecting mechanism is in the state that the extraction is completed, that is, the cutting head 5 is closed, the lowering of the patching button 13 is first pressed; if the connecting mechanism is in the state that the implanting is completed, that is, the cutter head 5 is opened, and the patching button 13 at the top is pressed first; if the connection mechanism is in the initial state, it is not necessary to press any button. Then, the groove structure under the connector 3 is clamped by the appliance, and then the connector 3 is inserted into the body mechanism so that the clamping key 33 is contracted while the clamp unit 35 is clamped to the cutter head 5. After reaching the targeted position, the fixture is used to clamp the protruding position and rotate. In the connecting head 3, the clamping key 33 is aligned with the hole of the second supporting frame, and the clamping key 33 is ejected by the spring 32 to re-fix the connection mechanism.

The invention claimed is:

1. An integrated device for hair follicle extraction and implanting, comprising:
   a body mechanism and a connecting mechanism, the body mechanism comprising a body supporting frame, a first motor, a transmission frame, a second motor, a clamping member, a transmission mechanism and a pushing needle;
   wherein the first motor is fixed inside the body supporting frame, the first motor is connected to the transmission frame;
   the second motor is fixed inside the body supporting frame, and a motor shaft of the second motor is connected to the pushing needle through the clamping member;
   the transmission mechanism comprises a sleeve and a clamping sleeve, the sleeve is connected with the clamping member, the sleeve is matched with the clamping sleeve in transmission process, and a gap capable of up-and-down movement is provided between the sleeve and the clamping sleeve;
   the connecting mechanism comprises a connecting head, a fixing head, and a cutter head, the connecting head is connected with the body supporting frame, and the fixing head is connected with the connecting head;
   the cutting head is hollow inside, and the pushing needle is placed in the cutting head, the cutting head penetrates through the connecting head and the fixing head, and an upper part of the cutting head is connected to the clamping sleeve;
   the sleeve is connected to the clamping sleeve, the first motor drives the cutter head to move up and down, and the second motor drives the rotary motion of the pushing needle and the cutter head.

2. The integrated device for hair follicle extraction and implanting as claimed in claim 1, wherein the first motor is a stepping motor, the second motor is a direct current brushless motor.

3. The integrated device for hair follicle extraction and implanting as claimed in claim 1,
   wherein the body supporting frame is divided into a first supporting frame and a second supporting frame connected to each other;
   the first motor is fixed in the first supporting frame by a fixing member, the second motor is fixed on the second supporting frame by a fixing scaffold;
   the connecting head is connected with the second supporting frame in the body supporting frame.

4. The integrated device for hair follicle extraction and implanting as claimed in claim 3, wherein the fixing member comprises two fixing units placed symmetrically, the first motor is sandwiched by the two fixing units, the fixing member is connected with the first supporting frame.

5. The integrated device for hair follicle extraction and implanting as claimed in claim 3, wherein a position limiting key is placed between the fixing scaffold and the second supporting frame.

6. The integrated device for hair follicle extraction and implanting as claimed in claim 5, wherein the transmission frame is hollow in a vertical direction, the position limiting key penetrates through a hollow part of the transmission frame to restrict a rotation of the transmission frame.

7. The integrated device for hair follicle extraction and implanting as claimed in claim 1, wherein the connecting head is in a flexible connection with the body supporting frame, the connecting mechanism is detachable from the body mechanism.

8. The integrated device for hair follicle extraction and implanting as claimed in claim 1, wherein the connecting head comprises an upper clamping unit, a spring and a clamping key, a lower clamping unit;
   the upper clamping unit is matched with the lower clamping unit and fixed inside the connecting head;
   the clamping key is sleeved with a spring, and the clamping key is fixed in a protruding position between the upper clamping unit and the lower clamping unit;
   an opening is formed in an outer wall of the body supporting frame, a protruding portion of the clamping key is clamped in the opening of the body supporting frame, which brings the clamping key in fixed connection with the connecting mechanism.

9. The integrated device for hair follicle extraction and implanting as claimed in claim 8, wherein a groove structure is provided at a periphery of the connecting head, and the groove structure is disposed at a joint part between the connecting head and the body supporting frame.

10. The integrated device for hair follicle extraction and implanting as claimed in claim 8, the connecting head further comprises a clamping unit, the clamping unit is disposed between the clamping key and the cutter head, and the clamping unit is connected to the clamping key, and the clamping unit clamps the cutter head as the clamping key is retracted.

11. The integrated device for hair follicle extraction and implanting as claimed in claim 1, an interior of the fixing head is of an inverted cone shape with a hollow structure and a wide upper portion and a narrow lower portion, a plurality of cutting edges are arranged at a lower part of the cutting head, and the plurality of cutting edges are bent towards inside of the cutting head.

12. The integrated device for hair follicle extraction and implanting as claimed in claim 1, wherein the sleeve is of an external spline structure, and an upper portion of the clamping sleeve is of an internal spline structure, and the clamping sleeve is in transmission match with the sleeve, and the lower portion of clamping sleeve is connected with the upper portion of the cutter head.

13. The integrated device for hair follicle extraction and implanting as claimed in claim 1, wherein the clamping sleeve is connected with an upper portion of the cutter head through a gear sleeve, and the gear sleeve is of an inner gear sleeve, the upper part of the cutter head is provided with a straight gear, and the inner gear sleeve is in meshed connection with the straight gear.

14. The integrated device for hair follicle extraction and implanting as claimed in claim 13, wherein the gear sleeve is made of an elastic material, the inner gear is of an inverted triangle shape, and top of the gear is rounded.

15. The integrated device for hair follicle extraction and implanting as claimed in claim 1, wherein the integrated device for hair follicle extraction and implanting further comprises a foot part switch and a hand part button, the foot part switch is provided at outside of the body mechanism to connect and control the second motor, the hand part button is provided on the body mechanism to connect and control the second motor.

\* \* \* \* \*